US006856397B2

(12) United States Patent
Huston et al.

(10) Patent No.: US 6,856,397 B2
(45) Date of Patent: Feb. 15, 2005

(54) SYSTEM AND METHOD FOR AUTOMATED FRINGE COUNTING USING IMAGE INFORMATION

(75) Inventors: Dryver R. Huston, S. Burlington, VT (US); Wolfgang Sauter, Burlington, VT (US); Peter A. Sonntag, Starnberg (DE)

(73) Assignee: The University of Vermont and State Agricultural College, Burlington, VT (US)

( * ) Notice: Subject to any disclaimer, the term of this patent is extended or adjusted under 35 U.S.C. 154(b) by 398 days.

(21) Appl. No.: 10/004,746

(22) Filed: Dec. 4, 2001

(65) Prior Publication Data

US 2002/0146151 A1 Oct. 10, 2002

Related U.S. Application Data

(60) Provisional application No. 60/251,065, filed on Dec. 4, 2000.

(51) Int. Cl.[7] ................................................ G01B 9/02
(52) U.S. Cl. ...................................... 356/450; 356/4.09
(58) Field of Search ............................... 356/450, 4.09, 356/FOR 107; 382/192, 199, 205, 282, 286, 311

(56) References Cited

U.S. PATENT DOCUMENTS

| | | | |
|---|---|---|---|
| 4,729,654 A | 3/1988 | Akuta et al. | 356/4.5 |
| 5,526,114 A | 6/1996 | Eselun | 356/345 |
| 5,546,184 A | 8/1996 | Downs | 356/345 |
| 6,050,138 A | 4/2000 | Lynch et al. | 73/150 |

OTHER PUBLICATIONS

*Bulge and Blister Testing of Thin Films and Their Interfaces*, Ph.D. Dissertation, Stanford University, by Robert J. Hohlfelder (1999); (specifically, pp. 95–120, Chapter 6, *It's a nice theory, but how do you run experiments?*)http://mse.stanford.edu/people/faculty/nix/people/past_members/rjhThesis/thesis.html.

*Application of Bulge Testing Techniques in Determining the Mechanical Properties of Thin Films*, Thesis by Jason Gill, University of Vermont (May, 1998).

*Automation of Temperature Measurement by Laser*, by Fei Yue, Xi Yangang, Chen Yuanjie, Ma Xiufang, Shen Yuanhua, Department of Physics, Fudan University, Shanaghai, China, Proceedings of SPIE, vol. 3558, pp. 87–92, *Automated Optical Inspection for Industry: Theory, Technology, and Applications II* (Aug., 1998).

*Primary Examiner*—Samuel A. Turner
(74) *Attorney, Agent, or Firm*—Downs Rachlin Martin PLLC

(57) ABSTRACT

A bulge testing system (10) for testing the material properties of a thin film window (14) using a Michelson interferometer (18) that generates an interference pattern (32) having fringes (34) and nodes (36) that move as the thin film window is inflated or deflated. The bulge testing system includes a fringe counting module (82), an analysis module (114) and an output module (88). The fringe counting module allows a user to interactively select from an image of the interference pattern one or more sampling regions (30) in which the user interface will count fringes. The analysis module allows a user to interactively change the location of maxima/minima indicators (116) in the event that noise in the image causes the analysis module to incorrectly determine the locations of the fringes and nodes. The output module automatically calculates material properties and provides test results to an output file and/or a results window (168).

63 Claims, 11 Drawing Sheets

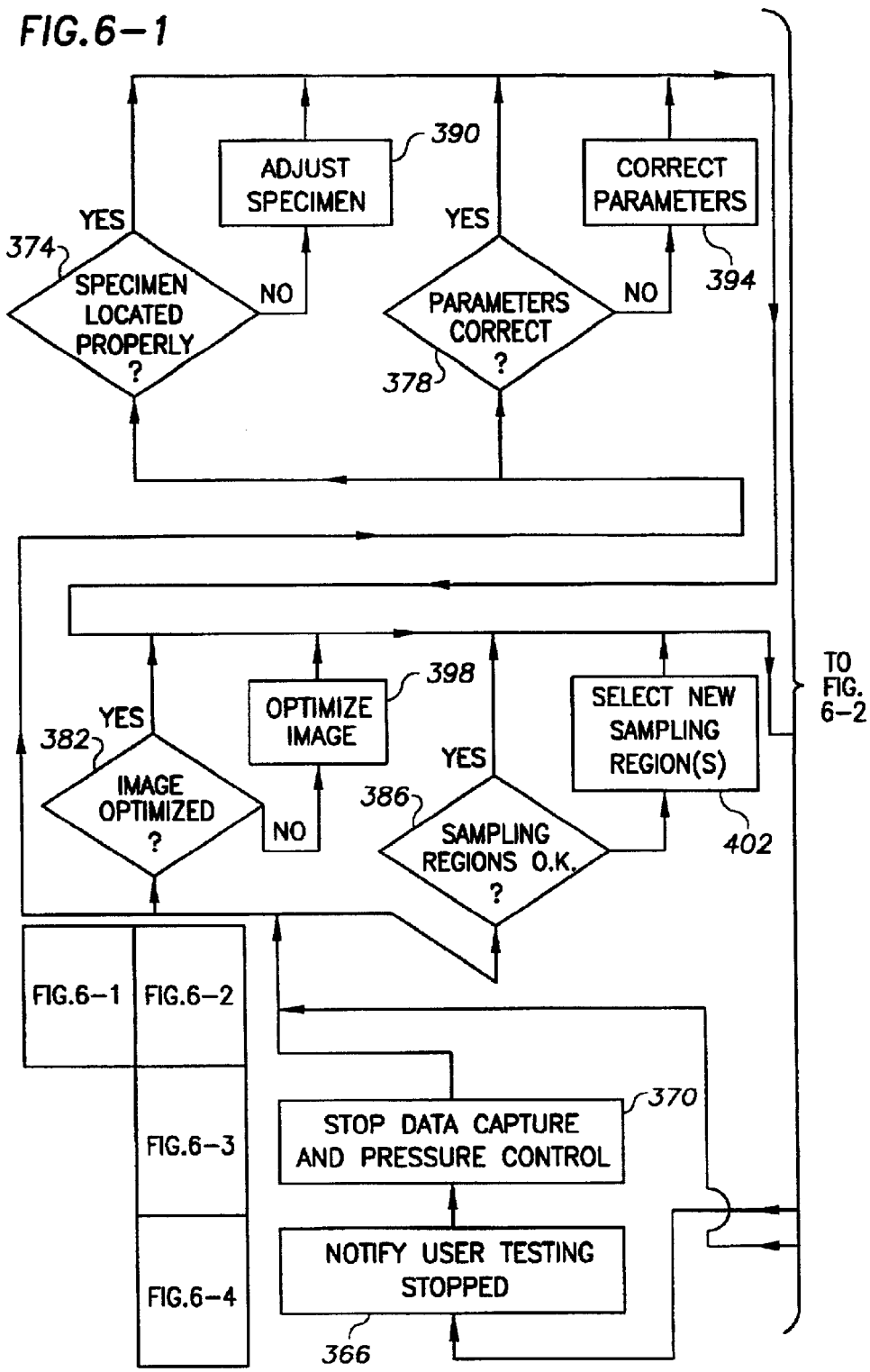

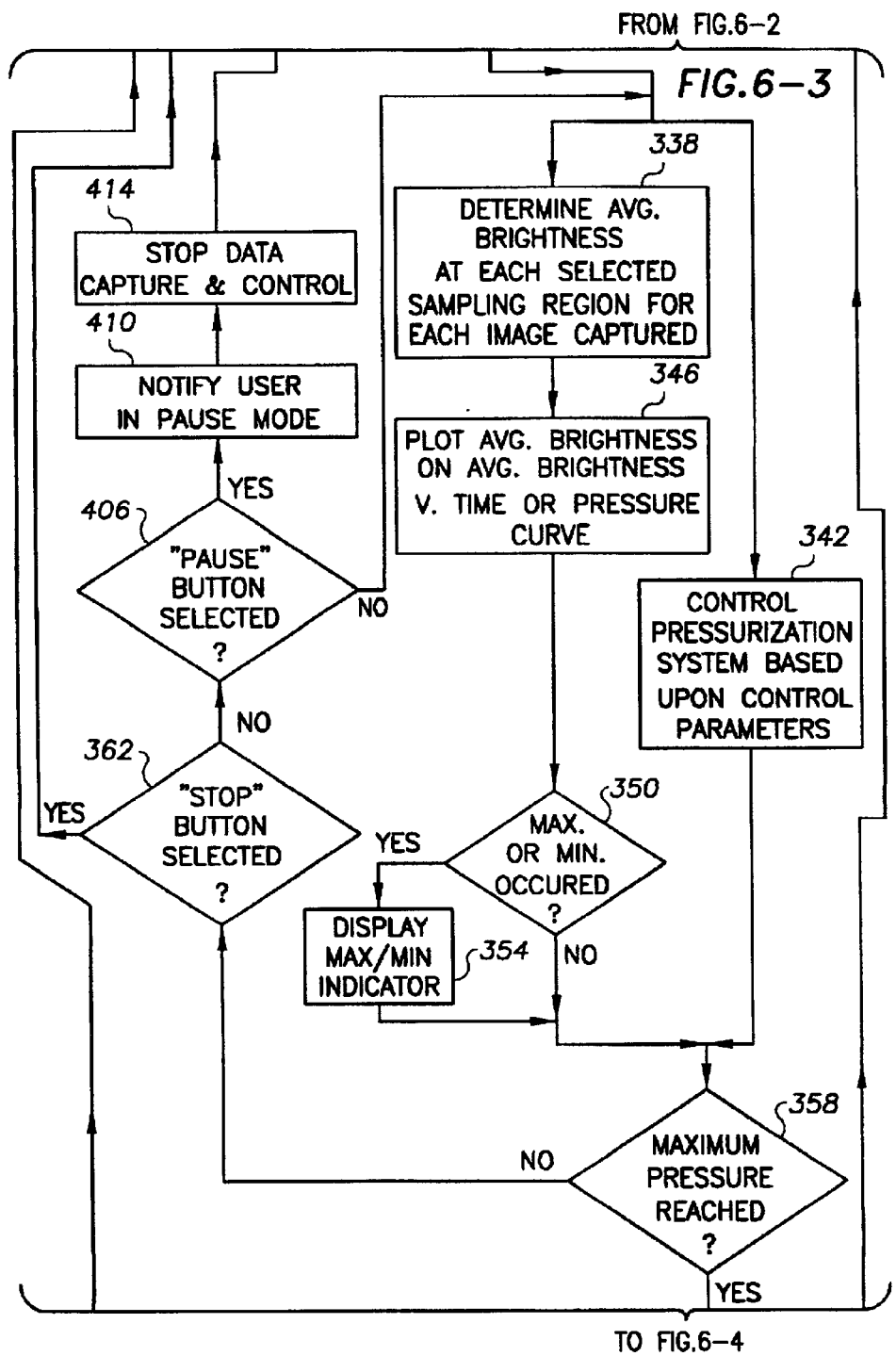

SYSTEM AND METHOD FOR AUTOMATED FRINGE COUNTING USING IMAGE INFORMATION

RELATED APPLICATION DATA

This application claims the benefit of U.S. Provisional Patent Application No. 60/251,065, filed Dec. 4, 2000, entitled "Automated Fringe Counting and Property Calculation System."

The invention described herein was funded in part by a National Science Foundation grant administered through the Vermont EPSCoR program, contract number EPS-9874685.

FIELD OF THE INVENTION

The present invention relates generally to the field of interferometry. More particularly, the present invention is directed to a system and method for automated fringe counting using image information.

BACKGROUND OF THE INVENTION

Interferometry has a number of useful applications including the measuring of displacements of various structures. For example, in the field of thin film mechanics, the well-known Michelson interferometer is often used in connection with bulge and blister testing, which are two conventional tests used to determine various material properties of thin films, such a Young's modulus, rupture strength, Poisson's ratio and adhesion, among others. In bulge testing, a test specimen may be created by first depositing a film to be tested onto a substrate, which is typically a silicon wafer having a silicon nitride layer on each of its front and back surfaces. Then, a window is created through the substrate by removing portions of the substrate using known masking and etching techniques.

To perform the bulge test, the specimen is placed onto a pressurization mount for applying a positive (or negative) pressure, relative to the ambient pressure, to the window. As the pressure is increased, the film window bulges in a direction away from the substrate, causing the film to displace by various amounts over the region of the window. By measuring the displacement of the film window and the pressure causing that displacement, and knowing the behavior of membranes under such loading conditions, several properties of the particular film may be calculated. Blister testing also utilizes a thin film window. However, instead of causing the film window to bulge only at the region of the window, the bulge is further pressurized to cause the film to delaminate from the substrate to determine the adhesion properties of the film.

Since the films tested using bulge and blister testing procedures are often very thin, e.g., on the order of 500 nm to 1,000 nm, and the corresponding displacements are also small, typically on the order of 10 $\mu$m to 100 $\mu$m, very precise displacement measurements are required. One known method of making such small, precise measurements is to use a Michelson interferometer in conjunction with a monochromatic laser light source. As is commonly known in the art, a properly-calibrated Michelson interferometer used for measuring the displacement of a bulging window produces an interference pattern consisting of alternating rings of fringes, i.e., regions of relatively intense light, and nodes, i.e., regions of relatively little or no light. The interference pattern is caused by constructive and destructive combination of a reference beam of the laser light reflected from a stationary mirror with a measuring beam of the laser light reflected from the bulge. As the bulge continues to displace away from the substrate, the fringes and nodes move outward from the center of the bulge as the measuring beam continuously shifts relative to the reference beam. Thus, to determine the displacement of the bulge between any two points in time, or pressures, the number of fringes (or nodes) passing a fixed point between those two times, or pressures, needs to be counted. The displacement may then be calculated by multiplying the number of fringes by one-half the wavelength of the light from the laser.

Presently, fringe counting is performed either manually, i.e., by projecting the interference pattern onto a screen and an observer viewing the screen and counting the number of fringes that pass a fixed reference point on the screen, or automatically, e.g., using a photodetector aimed at a fixed reference point to detect the alternating light intensities at the fixed reference point as the fringes pass by while the bulge is being inflated (or deflated). In conventional automated fringe counting systems, the photodetector is linked to a computer configured to graphically display the light intensity, time and/or pressure data on a computer screen.

These conventional fringe counting methods have an number of shortcoming. For example, in manual counting, it can be difficult for the observer to concentrate and remain focused on a fixed point throughout the entire test. Often, two people are used to manually count the fringes. One person observes the pattern and calls out when a new fringe passes the fixed point, and the other person records the passing of the new fringe. Manual counting is plagued by its relatively high potential for human error. Automated fringe counting eliminates many of the problems of manual counting, but the use of a photodetector creates some shortcomings of its own. For example, it can take a significant amount of time to properly aim the photodetector at the desire sampling point. In addition, typically a single photodetector is used to detect fringes at only a single sampling point. This, does not allow for redundancy and/or the detection of phenomena other than the passing of fringes past the sole reference point.

Other interferometry techniques may be used to measure the displacement of the bulge during bulge or blister testing. For example, instead of using a monochromatic laser, a white light diode may be used. In white light interferometry, the interference pattern generated by the interferometer is most intense when the distance the reference beam travels is equal to the distance the measuring beam travels. Thus, to determine displacement of the film at the bulge, it is necessary to move either the test specimen or the mirror reflecting the reference beam as the film displaces to make the travel lengths of the reference and measuring beams equal to one another. This requires the use of a precision movable stage and a corresponding control system that can add significantly to the cost and complexity of the bulge/blister testing apparatus.

BRIEF DESCRIPTION OF THE DRAWINGS

For the purpose of illustrating the invention, the drawings show a form of the invention that is presently preferred. However, it should be understood that the present invention is not limited to the precise arrangements and instrumentalities shown in the drawings, wherein:

FIGS. 3-1 to 3-3 show a screenshot of a control window of the user interface of FIG. 2;

FIGS. 6-1 to 6-4 show a flow diagram for using the user interface of FIG. 2 to bulge test a specimen.

SUMMARY OF THE INVENTION

In one aspect, the present invention is directed to a system for determining the movement of fringes and/or nodes of an interference pattern. The system comprises a detection device for capturing an image of the interference pattern. A user interface is in communication with the detection device for displaying to a user the image. A first module allows a user to interactively select at least one sampling region from the image, and a second module determines the passage of at least one of the fringes and nodes of the interference pattern through the at least one sampling region.

In another aspect, the present invention is directed to a system for determining the movement of fringes and nodes of an interference pattern through at least one sampling region. The system comprises a first module that displays at least one curve representing the movement of fringes and nodes of the interference through the at least one sampling region. A second module analyzes at least one characteristic of the curve and displays to a user results of the analysis. A third module allows a user to interactively change the results.

In a further aspect, the present invention is directed to a method determining the movement of fringes and/or nodes of an interference pattern. The method comprises the steps of capturing an image of the interference pattern and displaying the image on a display device. Then, at least one sampling region is interactively selected from the image displayed on the display device.

DETAILED DESCRIPTION OF THE INVENTION

Figure 1:
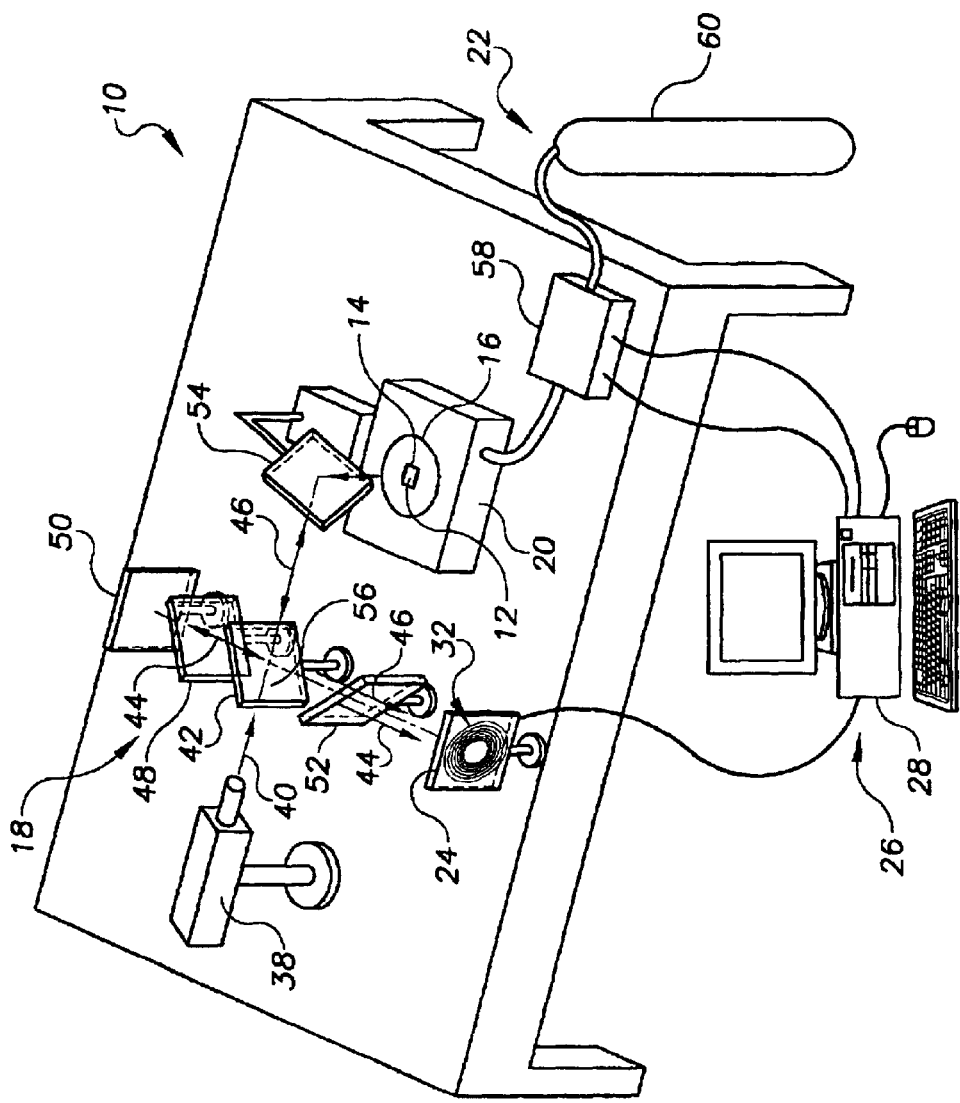
FIG. 1 is a perspective view of a bulge testing system of the present invention.

Referring now to the drawings, wherein like numerals indicate like elements, FIG. 1 shows in accordance with the present invention a bulge testing system, which is denoted generally by the numeral 10. As mentioned in the background section above, bulge testing system 10 may be used to determine various material properties of thin films. Thin films are used in a variety of devices, including microelectronic circuits, e.g., computer chips, optical coatings and protective wear-resistant coatings, e.g., bearing races. Manufacturers of thin film devices have a strong interest in determining the material properties of the films they use. This is so for both manufacturing process control and process development. Bulge testing system 10 may also be used for determining the strength of thin film windows, which is an emerging class of specialized structures that may have important industrial uses. Examples of applications for thin film windows include mask membranes for next generation lithography processes, diffusion barriers, radiation windows and pressure transducer membranes for microelectromechanical systems (MEMS).

Figure 2:
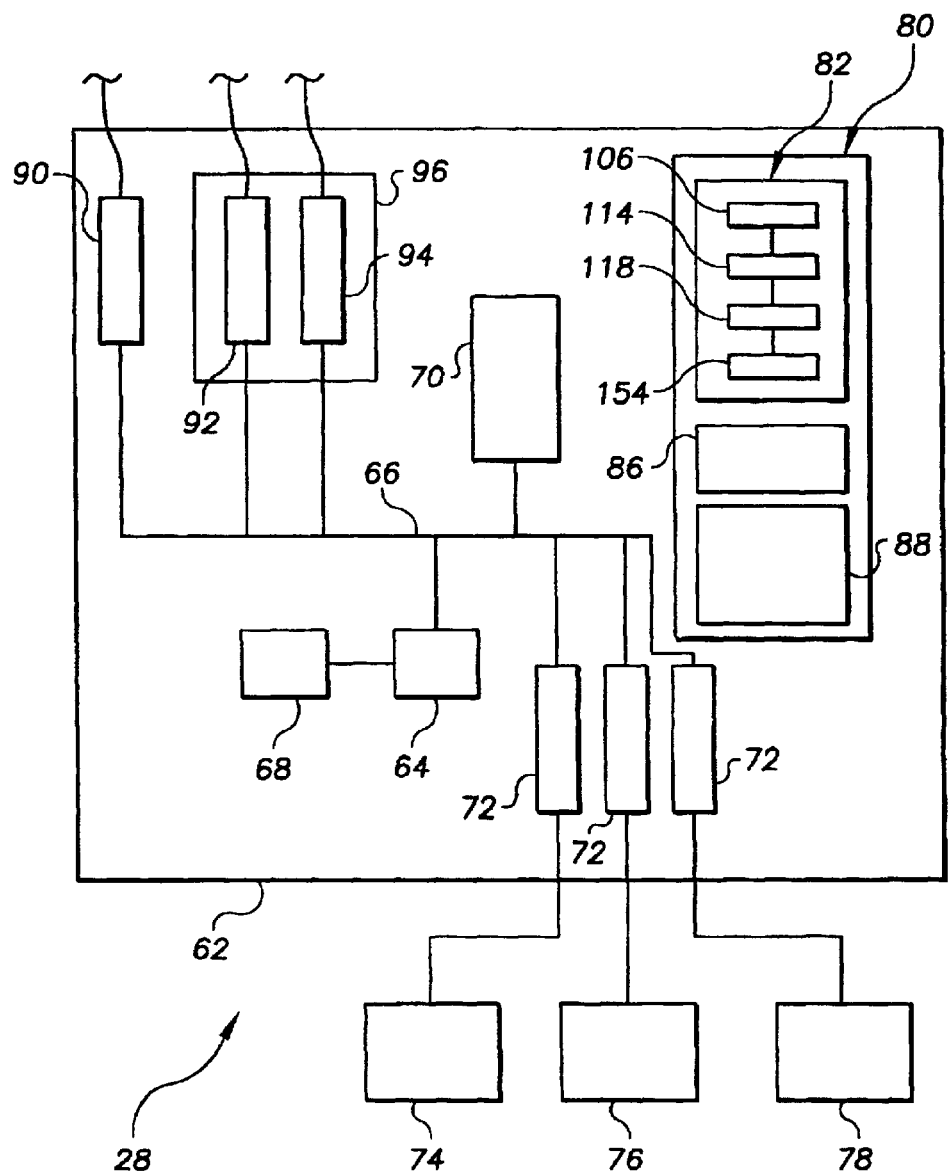
FIG. 2 is a schematic diagram of the user interface of the bulge testing system of FIG. 1.

Bulge testing system 10 may be used to determine the material properties of a thin film 12 at a film window 14 on a test specimen 16, which is often a wafer, such as a silicon wafer. Bulge testing system 10 may generally include a Michelson interferometer 18, a pressurization mount 20 for receiving test specimen 16, a pressurization system 22, an image detector 24 and a computer 26 for implementing a user interface 28 (FIG. 2). As discussed below in detail, user interface 28 may be used, among other things, to interactively control bulge testing system 10, collect and manipulate data during bulge testing and output test results, including automatically calculating one or more desired material properties. General details relating to bulge testing and test specimens are well known in the art and, therefore, are not discussed in detail herein. For more information regarding bulge testing, reference may be made to U.S. Pat. No. 6,050,138 to Lynch et al., which is incorporated herein by reference. As those skilled in the art will appreciate, the term "bulge testing" as used herein and in the appended claims, is intended to cover bulge testing, blister testing and any other testing in which an interferometer may be used to measure displacements.

Figures 1, 3:
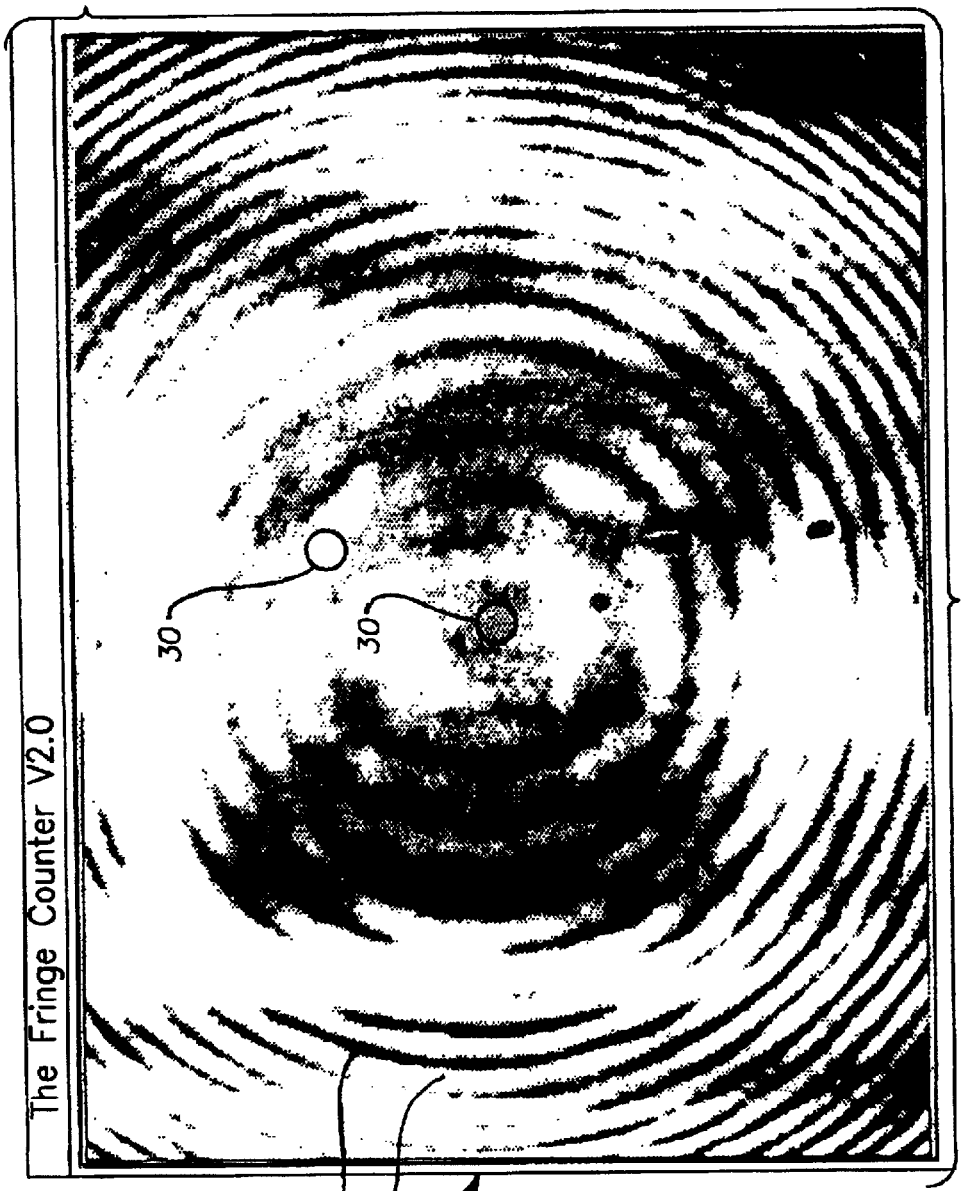
Figure 3:
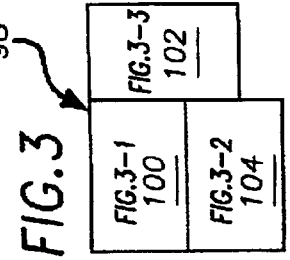
Figures 2, 3:
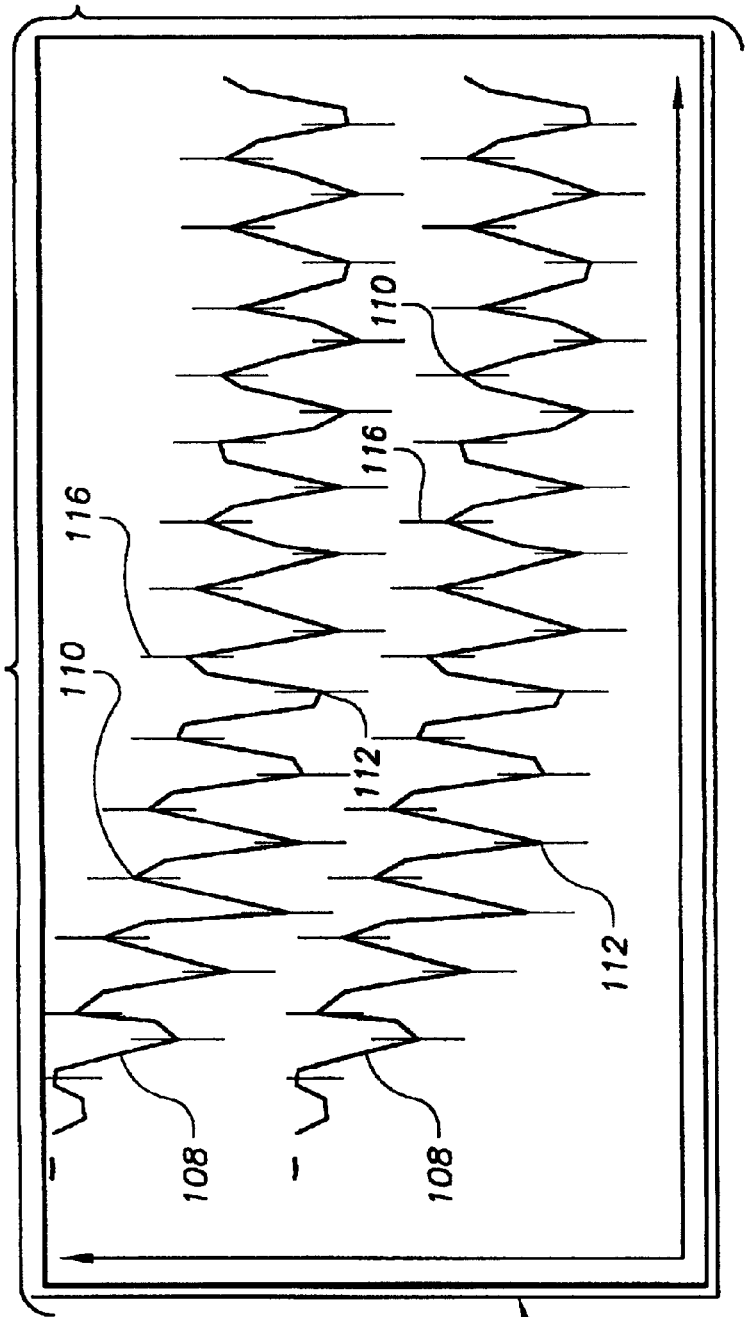
Figure 3:
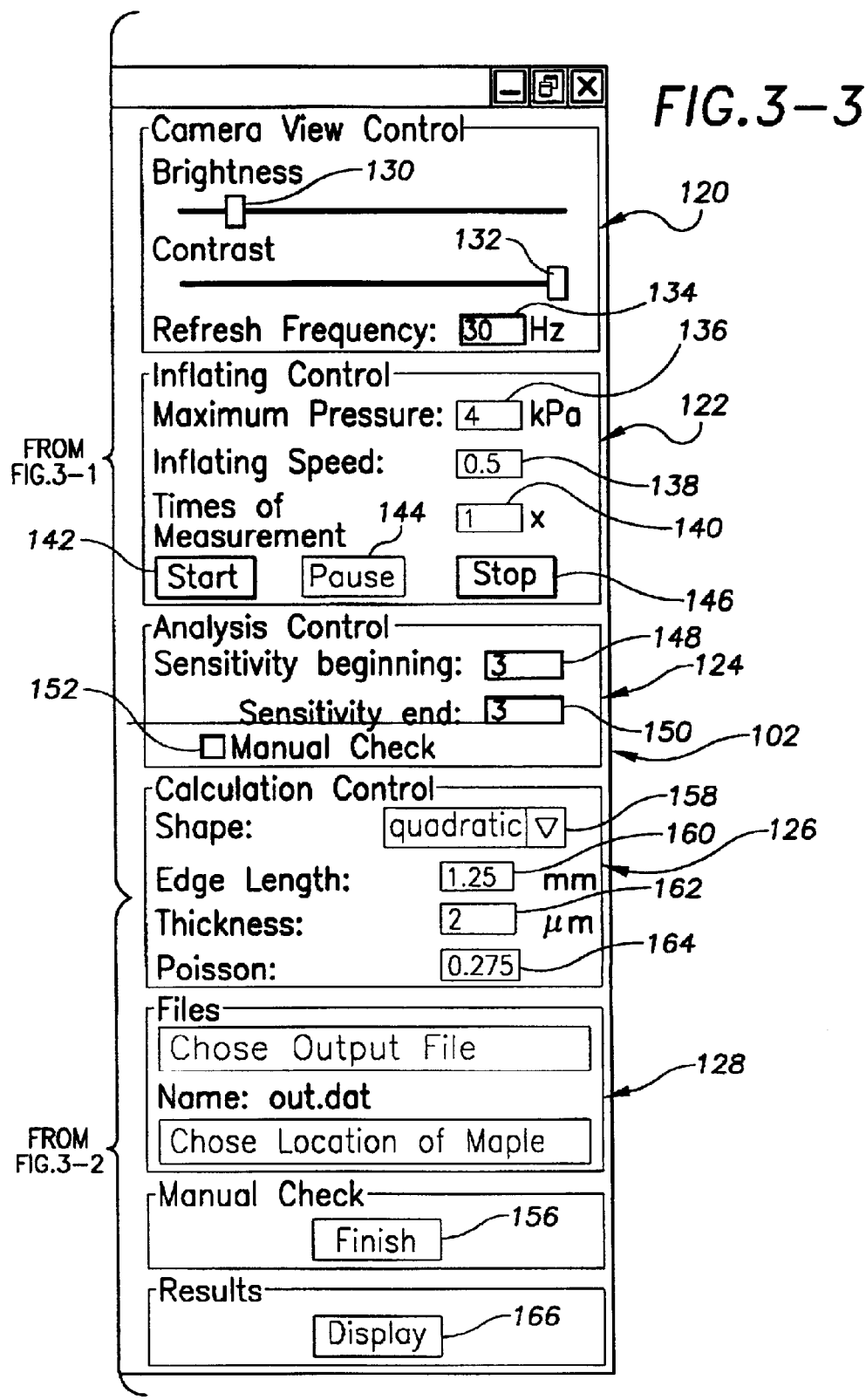

Referring to FIGS. 1 and 3-1, user interface 28, among other things, allows a user to interactively select one or more sampling regions 30 of an interference pattern 32 generated during the testing of specimen 16 for detection of the passing fringes 34 and nodes 36 of the interference pattern as the test proceeds. In addition, user interface 28 may permit a user to select the size(s) and/or shape(s) of the one or more sampling regions 30. Furthermore, user interface 28 may calculate various properties of the film being tested and graphically display various test data. These and other features of bulge testing system 10 of the present invention are described in detail below.

With continuing reference to FIG. 1, Michelson interferometer 18 includes a laser 38 for providing a beam 40 of monochromatic light. Laser 38 may be any laser that generates a monochromatic light beam, such as an HeNe laser or other laser generating a beam of relatively long coherence length light. Upon exiting laser, beam may pass through a beam splitter 42 that splits beam into a reference beam 44 and a measuring beam 46. Beam splitter 42 directs reference beam 44 through a first filter 48, such as a linear filter, toward a fixed reference beam mirror 50, which reflects the reference beam back through the beam splitter, through a second filter 52, which may also be a linear density filter, and to image detector 24. Beam splitter 42 directs measuring beam 46 to a mirror 54 that directs the measuring beam to film window 14 of specimen 16. Measuring beam 46 is then reflected from film window 14 back to mirror 54, which reflects the measuring beam to a mirrored surface 56 of beam splitter 42, which, in turn, reflects the measuring beam to image detector 24. Measuring beam 46 combines constructively and destructively with reference beam 44 to form interference pattern 32 at image detector 24. As discussed in the background section above, as thin film window 14 inflates and deflates, fringes 34 (FIG. 3-1) and nodes 36 of interference pattern 32 appear to move, respectively, outward or inward relative to the center of the interference pattern.

Pressurization mount 20 may have one or more orifices (not shown) for pressurizing film window 14 during testing. Each orifice may be in fluid communication with pressurization system 22, which in the embodiment shown is a positive pressure system that includes a mass flow controller 58 and a source 60 of pressurized fluid, e.g., nitrogen or air, among others. Pressurization system 22 may also include a pressure relief valve (not shown), a second mass flow controller (not shown) or other means for deflating film window 14. Those skilled in the art will appreciate that pressurization system 22 may be any positive pressure, vacuum or other displacement system commensurate with the test being performed. For example, mass flow controller 58 and its corresponding pressure source 60 may be replaced by a pressure or vacuum pump, such as a piston-type or other pump.

Image detector 24 may be a digital camera, such as a CCD, e.g., model no. XC-75, available from Sony Corporation of America, New York, N.Y., or CMOS camera, or other image capturing device, and is preferably located and/or configured such that entire film window 14 of specimen 16 is visible within the imaging area of the image detector. However, image detector 24 may located and/or configured such that its imaging area contains only a portion of film window 14, such as a central portion of interference pattern 32.

User interface 28 may be implemented on computer 26, which may be a personal computer, such as a Pentium® or PowerPC® based or similar personal computer. (Pentium is a registered trademark of Intel Corporation, Santa Clara, Calif., and PowerPC is a registered trademark of International Business Machines Corporation, Armonk, N.Y.) Those skilled in the art, however, will recognize that user interface 28 may alternatively be implemented on another computer system, such as a dedicated bulge testing workstation, mainframe or a distributed computer network.

Referring to FIG. 2, when user interface 28 is implemented on multipurpose personal computer 26 (FIG. 1), the user interface may include a central processing unit (CPU) 62 that includes a microprocessor 64, a data bus 66, RAM 68, persistent read/write memory 70, such as a hard drive, and a number of peripheral device drivers 72 for operating peripheral devices, such as a monitor 74, a keyboard 76 and a pointing device 78, such as a mouse.

CPU 62 may also include user interface software 80, which may reside in RAM 68 and/or persistent memory 70, for providing user interface 28 with its functionality. For example, software 80 may include various modules, such as a fringe counting module 82, a pressurization system control module 86 and a data output module 88 for presenting test data and/or film material properties to a user, e.g., by writing such information to an output file or displaying the results on monitor 74. Each of these and other modules are discussed below in detail. As those skilled in the art will readily appreciate, the term "module" as used herein and in the appended claims is generally used to denote functionality, regardless of the structure of the software code, i.e., regardless of whether or not the software code is composed of distinct sections each corresponding to a particular functional module. The term "module" also includes any hardware required to implement the corresponding functionality of user interface 28.

CPU 62 may further include one or more plug-in cards or other interfaces for receiving data from and/or providing information to various components of bulge testing system 10. For example, CPU 62 may contain a framegrabber card 90, such as an Imagenation PXC200 Frame Grabber, available from CyberOptics Corporation, Minneapolis, Minn., that is in electrical communication with image detector 24 for capturing therefrom an image of interference pattern 32 at a particular instance of time for use by fringe counting module 82. If mass flow controller 58 is analog, CPU 62 may contain an analog to digital converter (ADC) 92 card for communicating data from the mass flow controller to the CPU for use in user interface 28. Similarly, if mass flow controller 58 is analog, a digital to analog converter (DAC) 94 may also be provided for providing a control signal from pressurization system control module 86 to the mass flow controller. ADC 92 and DAC 94 may be provided on a common plug-in card 96, such as a PCI-6023E I/O card available from National Instruments Corporation, Austin, Tex. Those skilled in the art will readily appreciate that there are many ways to implement the present invention with various types and combinations of analog and digital equipment and corresponding computer interfaces. A recitation of numerous configurations is not necessary for an understanding of the scope of the claims appended hereto.

For an understanding of the function of user interface 28 and the various software modules thereof, reference should now be made to FIG. 3 in conjunction with FIG. 2. FIG. 3 is a screenshot of a control window 98 of user interface 28 that would typically be displayed on monitor 74 during the performance of a bulge test. Control window 98 generally includes an image frame 100, a controls region 102 containing various controls for controlling various functions of user interface 28 and bulge testing system 10, and a graph frame 104.

Image frame 100 displays bitmapped images of interference pattern 32 captured by framegrabber card 90 from image detector 24. As mentioned above, image detector 24 may provide an image containing entire film window 14 of specimen 16. Accordingly, image frame 100 may display the entire image captured by image detector 24 and, therefore, entire film window 14. Prior to starting a bulge test, fringe counting module 82 allows a user to select one or more sampling regions 30 at any location(s) within image frame 100. The user may select the one or more sampling regions 30 using any of a number of methods known in the art, such as using pointing device 78 to define the location, shape and/or the size of each sampling region. For example, fringe counting module 82 may include a sampling region selection module 106 that provides the user with a pop-up menu (not shown) of various shapes for sampling regions 30 from which the user may select. Sampling regions 30 may be displayed in image frame 100 as outlined or filled areas. Such selection techniques are analogous to shape drawing features of various drawing and painting computer applications/modules such as MicroSoft Paint, available from Microsoft Corporation, Redmond, Wash., and AppleWorks, available from Apple Computer, Inc., Cupertino, Calif. Each sample region 30 defines the bitmap region within image frame 100 that fringe counting module 82 uses to "count" fringes 34 and nodes 36 of interference pattern 32.

Experience has shown that if only one sampling region 30 is selected, the optimal location for it may be the center of interference pattern 32. The center appears to be least affected by secondary interference patterns that may develop during testing due to localized irregularities of the shape of the bulge formed at film window 14 and other factors. In addition, present experience appears to indicate that the optimal shape of each sampling region 30 is circular, and the optimal diameter of the circle is substantially equal to the width of each fringe 34 in a direction radial to the center of interference pattern 32. Using more than one sampling region 30 can provide a number of benefits over using a single sampling region. Such benefits include redundancy, determining and rejecting local disturbances and determining the direction in which fringes 34 are moving.

During a bulge test, fringe counting module 82 senses the passage of fringes 34 and nodes 36 through each sampling region 30. Those skilled in the art will appreciate that, depending upon the size(s) of sampling region(s) 30, any of a variety of image recognition algorithms may be used to detect fringes 34 and nodes 36. When sampling region 30 is a circle having a diameter generally no greater than the width of each fringe 34, fringe counting module 82 may determine the passage of the fringes and nodes 36 by determining the brightness of the pixels within the bitmap of the corresponding sampling region, e.g., by averaging the brightness of all pixels within that sampling region in a manner known in the art. Fringe counting module 82 may then display within graph frame 104 a curve 108 of average brightness versus time and/or average brightness versus pressure for each sampling region 30.

Each curve 108 may be display within a single graph frame 104 as shown, e.g., by displaying the curves in different colors corresponding to like-color coded sampling regions, or otherwise denoting which curve corresponds to which sampling region. Alternatively, each curve 108 may be presented in its own graph frame (not shown). If the bulge test proceeds properly, curve(s) 108 of average brightness versus time (or pressure) will contain a number of peaks 110 and valleys 112 representing, respectively, the relatively bright fringes 34 and relatively dim nodes 36 of interference pattern 32. It is noted that brightness curves 108 are shifted away from a level of zero brightness due to ambient light and/or other noise within the image of interference pattern 32 displayed within image frame 100.

Fringe counting module 82 may include an analysis module 114 for visually identifying to a user in graph frame 104 the locations of maxima and minima average brightness on each brightness curve 108. For example, fringe counting module 82 may display an indicator 116, such as a vertical line, at each maximum and minimum. The determination of the maxima and minima by analysis module 114 may be accomplished in a number of ways, including implementing a known edge detection or curve-following algorithm or the like that determines where each curve 108 reverses direction, such as occurs at points of maximum and minimum average brightness.

If bulge test system 10 is operating properly, the maxima and minima detected by analysis module 114 should correspond, respectively, to fringes 34 and nodes 36. By displaying the locations of maxima and minima via indicators 116, a user can quickly determine whether or not the bulge test was performed properly. If too much noise exists, local disturbances may cause the particular maxima and minima detection algorithm to display indicators 116 in incorrect locations and/or miss one or more fringes 34 and/or nodes 36 entirely. As described in more detail below, fringe counting module 82 may include a manual adjustment module 118 that allows a user to interactively change the location of, or eliminate, one or more of the incorrectly located indicators 116.

With continuing reference to FIG. 3, controls region 102 may contain an image view control region 120, an inflation control region 122, an analysis control region 124, a calculation control region 126 and a files region 128, each of which is described in detail below.

Image view control region 120 may include one or more controls, e.g., a brightness control 130 and a contrast control 132, for controlling various characteristics of images captured by framegrabber card 90 (FIG. 2) as displayed in image frame 100 and used by fringe counting module 82 (FIG. 2). Brightness control 130 and contrast control 132 allow a user to adjust the image so as to reduce as much noise as possible from the images so that average brightness curve 108 likewise contains as little noise as possible. Controls 130, 132 may control the corresponding functions on image detector 24 itself or on framegrabber card 90, depending upon the particular image detector and framegrabber card used. Image view control region 120 may also include a "Refresh Frequency" control 134 that allows a user to control the frequency at which framegrabber card 90 captures images from image detector 24 and refreshes image frame 100. A user may wish to vary the capture frequency to increase the number of datapoints for plotting the corresponding brightness curve 108, adjust the capture frequency to changes to the rate of inflation of film window 14 (FIG. 1) or the like.

Inflation control region 122 may be provided to allow the user to interactively input parameters for controlling the pressurization of thin film window 14 (FIG. 1). Accordingly, inflation control region 122 may include a "Maximum Pressure" control 136 for controlling maximum pressure, e.g., to prevent film window 14 from bursting, an "Inflation Speed" control 138 for controlling the rate of pressure increase beneath the film window and a "Times of Measurement" control 140 for controlling the number of times pressure data from mass flow controller 58 is collected, e.g., relative to the frequency that framegrabber card 90 captures images and fringe counter module 82 determines the average brightness at each sampling region 30.

In addition, inflation control region 122 may also include controls, such as a "Start" button 142, "Pause" button 144 and "Stop" button 146, which may control not only the operation of pressurization system 22, but also the functioning of fringe counting module 82 with respect to the capturing of images and analysis of average brightness. For example, when a user selects "Stop" button 146, fringe counting module 82 may stop framegrabber card 90 from capturing images and stop determining the average brightness within each sampling region 30. In addition, selection of "Stop" button 146 may reset fringe counting module 82 so that sampling region selection module 106 is again active to allow the user to reselect one or more sample regions 30, if desired. Sampling region selection module 106 may also be reactivated immediately after the pressure indicated in the "Maximum pressure" control 136 has been reached. Selection of "Start" button 142 may deactivate sampling region selection module 106 and initiate pressurization by pressurization system 22, image capturing by framegrabber card 90 and average brightness analysis and plotting of average brightness curves 108. Selection of "Pause" button 144 may merely suspend pressurization, frame capturing and average brightness analysis.

Analysis control region 124 may contain controls for controlling the algorithm of analysis module 114 that automatically determines and places visual indicators 116 at the locations of the maxima and minima of each brightness curve 108. As mentioned above, this algorithm may be an edge detection algorithm or curve following algorithm that follows the curve and detects a changes in its direction. The algorithm may detect a maximum or minimum by observing whether or not a certain number of pixels (or groups of pixels) on curves 108 on one side of a particular pixel extend vertically in one direction while a certain number of pixels on the curve on the other side of that particular pixel extend vertically in the same direction. If so, the algorithm may determine it has detected a maximum or a minimum, depending upon which vertical direction the pixels extend, and analysis module 114 may plot a corresponding indicator 116. Accordingly, analysis control region 124 may contain a "Sensitivity beginning" control 148 and a "Sensitivity end" control 150 that allow a user to select the number of pixels (or groups of pixels) to consider in determining locations of maxima and minima.

For example, certain disturbances in the images of interference pattern 32 may occur that cause small upward spikes (not shown) on an average brightness curve 108 between each maxima and minima such that the spikes that have one leg three pixels long and the other leg greater than three pixels long. If "Sensitivity beginning" control 148 and "Sensitivity end" control 150 are set to a value of three or fewer pixels, the maxima/minima detection algorithm will indicate that the local spikes are maxima. This will cause errors in subsequent displacement calculations due to the presence of additional maxima that do not actually correspond to fringes 34. However, by changing one, the other or both of "Sensitivity beginning" and "Sensitivity end" controls 148, 150 to a value of at least four, depending upon the locations of the spikes, the maxima/mimima detection algorithm will no longer detect the offending spikes.

Analysis control region 124 may also include a "Manual Check" control 152 that allows a user to initiate an edit module 154 that permits the user to move and/or eliminate indicators 116 that appear to the user to be improperly located and/or to add new locators to locations that were entirely missed by the maxima/minima algorithm. For example, one or more indicators 116 may be moved using various selection and "drag and drop" techniques know in the art. Similarly, one or more indicators may be eliminated by dragging the indicator(s) out of graph frame 104. Indicators 116 may be added, e.g., by "right-clicking" on mouse 78 (FIG. 2) to cause new indicator to appear, and then dragging and dropping the indicator to its desired location. When the user is finished manually checking and updating the locations of the maxima and minima, the user may then select a "Finish" button 156 that may be present in controls region 102. Selecting "Finish" button 156, may exit edit module 154.

Calculation control region 126 may contain several controls for setting parameters that output module 88 may use to calculate the material properties of thin film 12 after average brightness and pressure data has been captured and stored. For example, calculation control region 126 may contain a "Shape" control 158 that allows a user to select the polynomial order of the equation used to curve fit a displacement versus pressure diagram, which is described in more detail below. Calculation control region 126 may also contain an "Edge Length" control 160, a "Thickness" control 162 and a "Poisson" control 164 that allow a user to input, respectively, the edge length of a square window of specimen 16, the thickness of film window 14 and the value of Poisson's ratio for the particular type of film 12 being tested. It is noted that user interface 28 described herein is particularly configured for testing specimens having square windows. Hence, a user need input only a single edge length. However, if film window 14 were rectangular, calculation control region 126 may have controls (not shown) that allows a user to input the two different edge lengths. Similarly, if film window 14 were circular, calculation control region 126 may contain a control (not shown) that allows the user to input the diameter of the window. Of course, other shapes for film window are possible. Therefore, calculation control region 126 may contain other controls that allow the user to input other parameters necessary for output module 88 to calculate the desired material properties.

File region 128 contains various controls that allow a user to select a particular output file to which output module 88 outputs the results of the test. Those skilled in the art will readily understand such file control. Thus, further explanation of file region 128 is not required.

Figure 4:
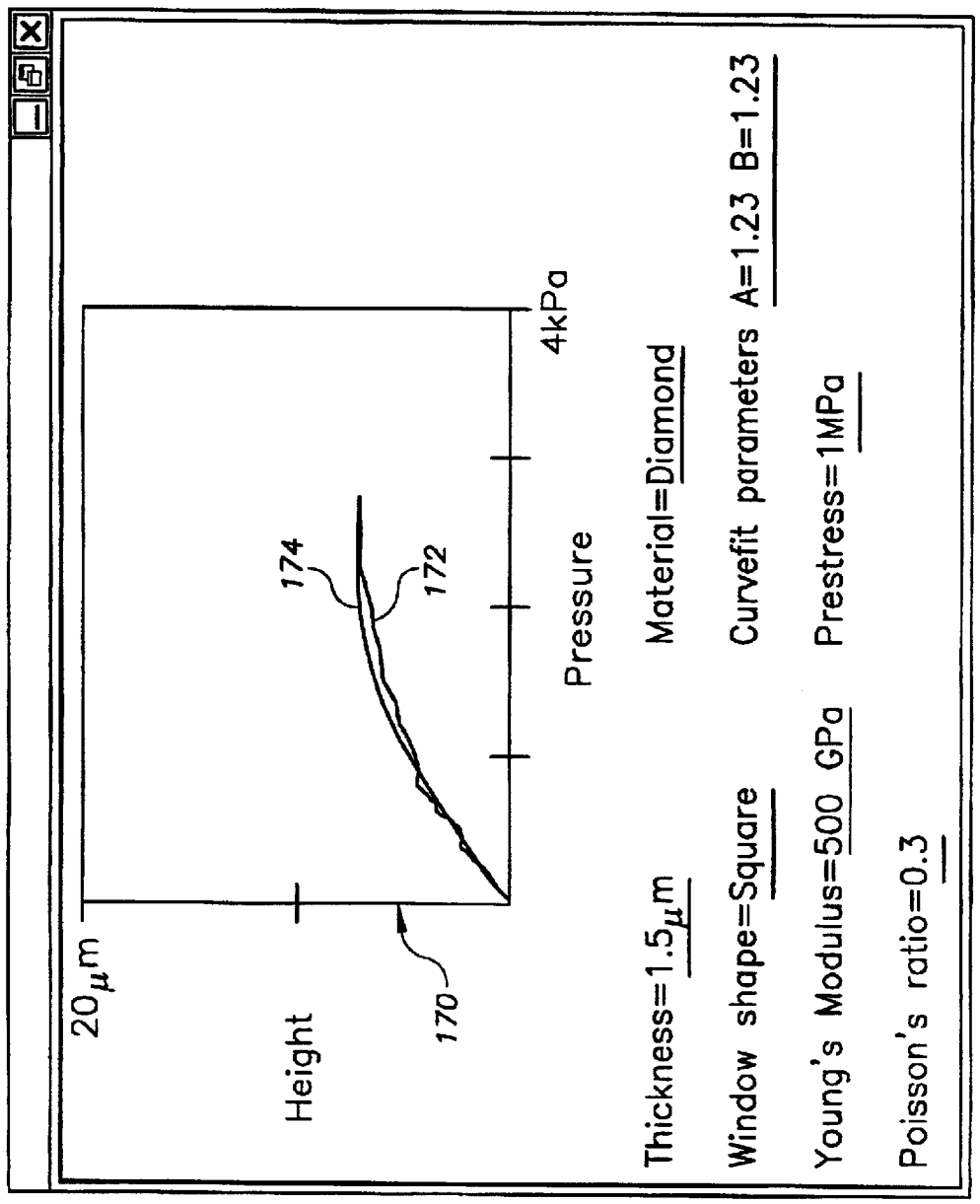
FIG. 4 is a screenshot of a results window of the user interface of FIG. 2.

Controls region 102 may also contain a "Display" button 166 or other means for displaying results calculated by output module 88. After a bulge test has been performed successfully, a user may select "Display" button 166 to display the results of the test, e.g., in a results window 168 (FIG. 4) presented on monitor 74 (FIG. 2). As shown in FIG. 4, while also referring to FIG. 3, results window may include a graph 170 of a displacement, or height of bulge, versus pressure curve 172, one or more properties calculated by output module 88, e.g., Young's modulus and prestress and other information such as the thickness provided in "Thickness" control 162, the shape of film window 14 (FIG. 1) Poisson's ratio as provided in "Poisson's" control 164, the material type of the film tested and/or curvefit parameters, among others. If user does not select "Display" button 166 after performing a test, all of the information that would have been displayed in results window 168 may be written to an output file, such as may be selected in file region 128.

Graph 170 may include a fitted curve 174 fit to the displacement versus pressure curve 172 by output module 88. Fitted curve 174 may be based on either the polynomial selected in "Shape" control 158 of calculation control region 126 or a default polynomial. For example, the default polynomial may be a cubic polynomial having the form:

$$p = Ah^3 + Bh \quad \{1\}$$

where "p" is the pressure, "h" is the height, or displacement, of film window and "A" and "B" are constants. For a square membrane, constants "A" and "B" are:

$$A = \frac{1}{(0.801 + 0.061v)^3} \frac{Et}{a^4(1-v)} \quad \{2\}$$

$$B = \sigma_0 t / a^2 \quad \{3\}$$

where "E" is Young's modulus, "t" is the thickness of film window 14, "a" is the edge length of the film window, "v" is Poisson's ratio and "$\sigma_0$" is the prestress in the film window. For film windows of other shapes, the values of "A" and "B" are different. By algebraically manipulating equations {1}, {2} and {3}, e.g., output module 88 may determine Young's modulus and the prestress within film 12 at film window 14. Those skilled in the art will recognize that other equations and other manipulations may be made to determine other material properties. The various equations for determining various properties of thin film windows using bulge testing procedures and various algorithms for manipulating these equations are know in the art. Therefore, a detailed discussion of such equations and algorithms herein is not required.

Figure 5:
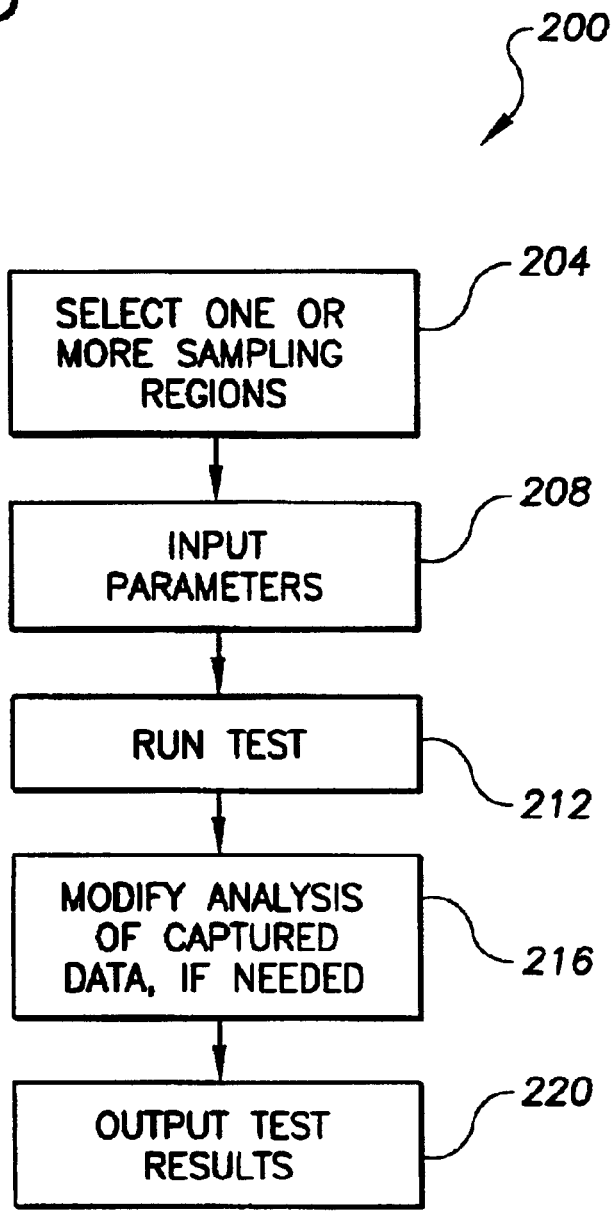
FIG. 5 is a flow diagram showing an overview of the user interface of FIG. 2.

FIG. 5 is a flow diagram 200 presenting an overview of user interface 28 (see FIGS. 2 and 3) of the present invention. At step 204, a user may select one or more sampling regions 30 from the image of interference pattern 32 displayed in image frame 100 of control window 98. After the user has selected the desired sampling regions 30, at step 208, the user may input the variables necessary for user interface 28 to perform the test, analyze the data captured during the test and report the test results to the user. Then, at step 212, the user may run the test using user interface 28 to initiate and otherwise control the testing process. As mentioned above, although user interface 28 is presented in the context of bulge testing system 10, the user interface may be used with virtually any test that utilizes data regarding the passage of fringes 34 and/or nodes 36 through one or more sampling regions 30.

The analysis module 114 of user interface 28 analyses data captured during the test and provides visual indicators 116 that allows the user to see where the analysis has detected maxima and minima on the one or more average brightness curves 108. At step 216, user interface 28 may allow the user to interactively make changes, if needed, to the analysis of captured data prior to the data being used to perform various calculations for reporting results to the user. At step 220, user interface 28 may provide test results to the user, e.g., by writing the results to an output file or displaying the results to monitor 74 or other output device. Details of steps 204–220 in the context of one embodiment of bulge testing system 10 are presented below in FIG. 6 and related text.

Figures 2, 6:
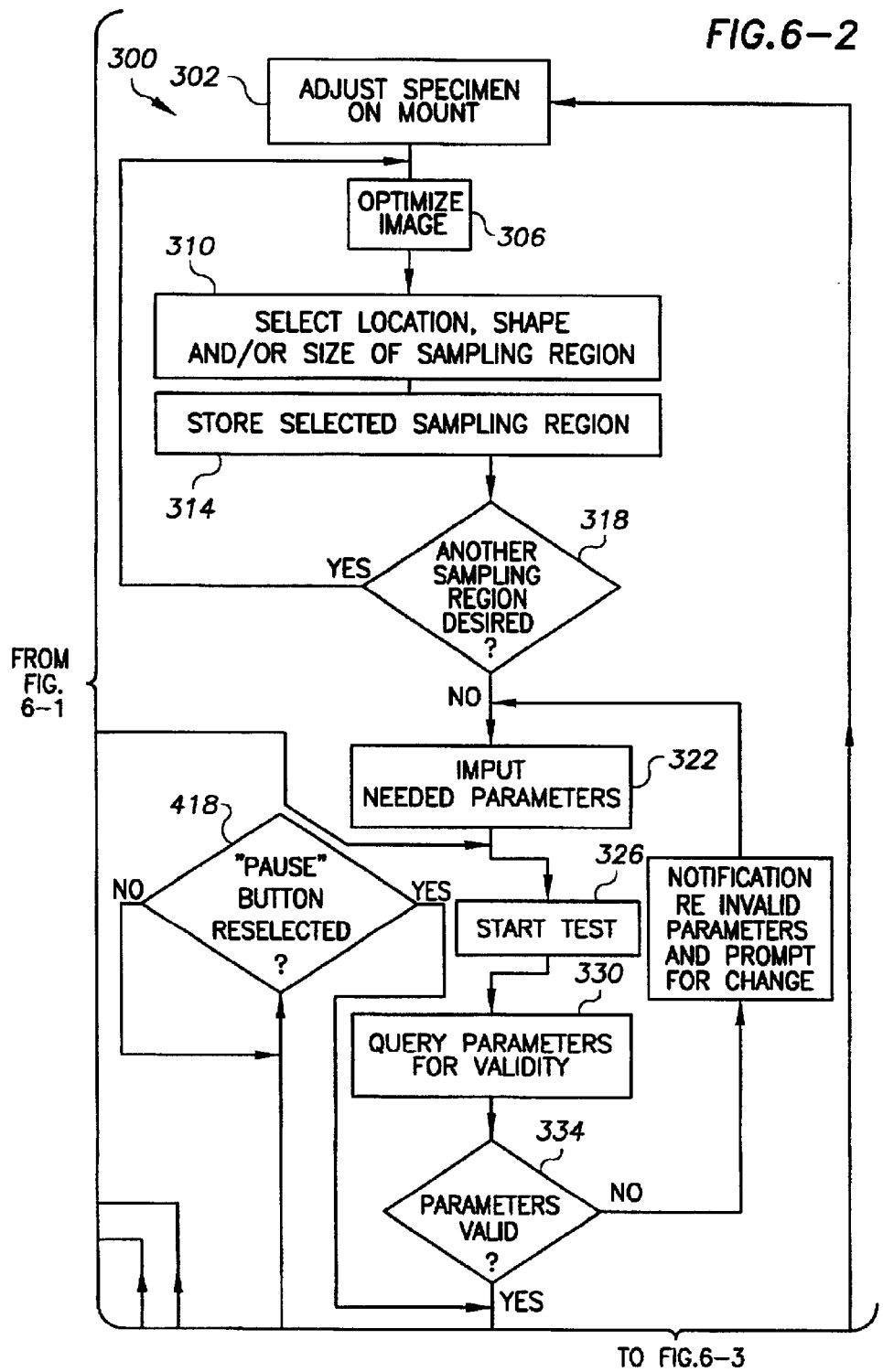
Figures 4, 6:
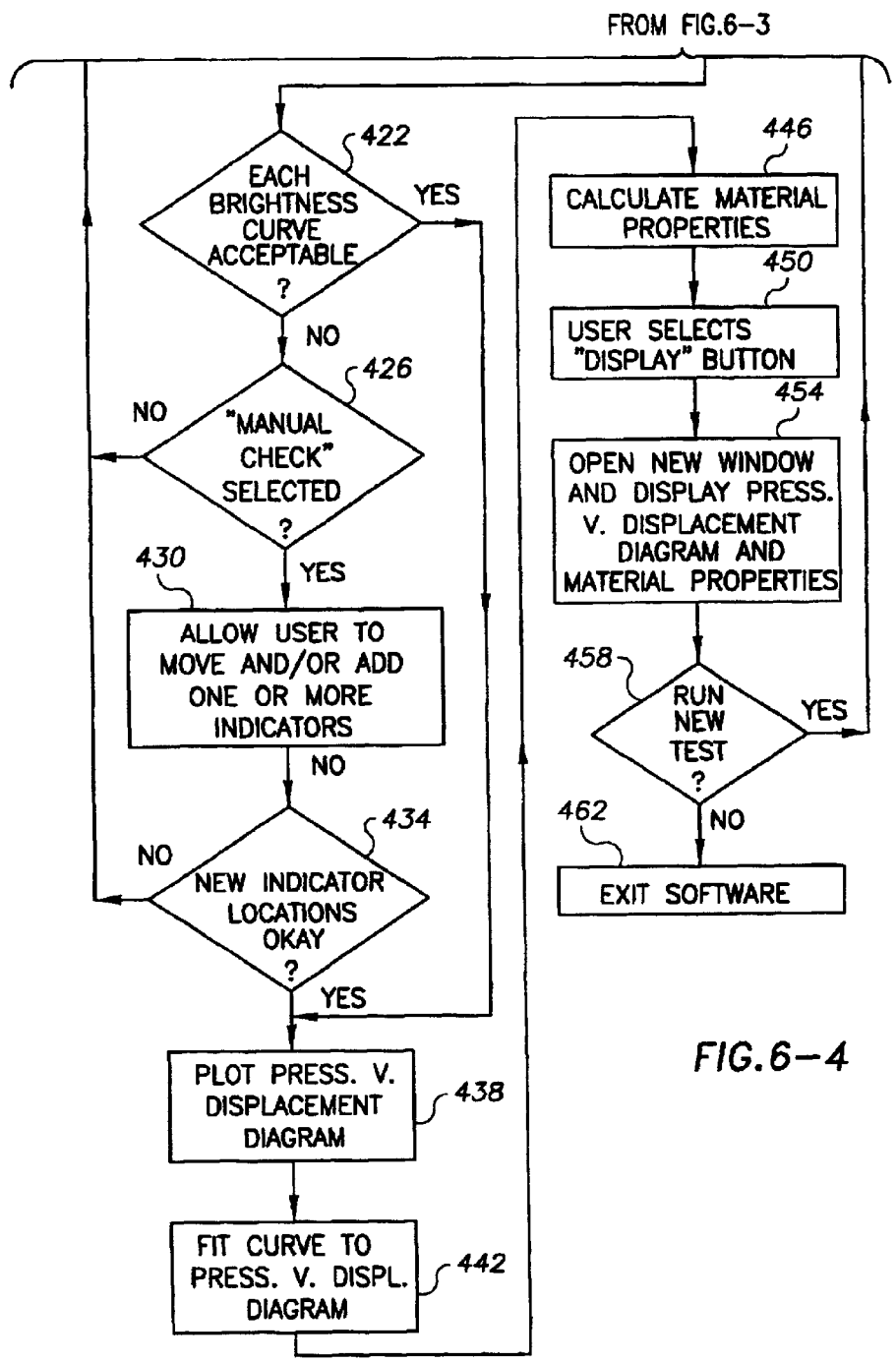

Referring now to FIG. 6, which shows an exemplary flow diagram 300 for conducting a bulge test using bulge testing system 10 of the present invention, and also FIGS. 1, 2, 3 and FIG. 4 as required, at step 302, a user may place a new specimen and/or adjust an existing specimen on pressurization mount so that measuring beam is centered on film window. At step 306, the user may optimize the image characteristics, e.g., brightness and/or contrast using brightness control 130 and/or contrast control 132, of the image displayed in image frame 100 as needed to reduce image noise to improve the results of the fringe detection algorithm. At step 310, user may then use mouse 78 to select a desired location, shape and/or size of a sampling region 30. Fringe counting module 82 then stores at step 314 information regarding the location of selected sampling region 30 for use in determining the average brightness of that region during the test. At step 318, if desired, the user may continue to select one or more sampling regions 30 in which fringe counting module 82 will count fringes.

At step 322, when the user has selected the desired one or more sampling regions 30, the user may then input all of the necessary parameters needed to perform the bulge testing using, e.g., "Refresh Frequency" control 134, "Maximum Pressure" control 136, "inflating Speed" control 138, "Times of Measurement" control 140, "Sensitivity beginning" control 148, "Sensitivity end" control 150, "Manual Check" control 152, "Shape" control 158, "Edge Length" control 160, "Thickness" control 162 and "Poisson" control 164. Those skilled in the art will appreciate that the parameters shown are only exemplary and that other parameters may be used, depending upon the type of test being performed.

After inputting the necessary parameters, at step 326, user may then start a test by selecting "Start" button 142 or other mean for initiating the test. Then, at step 330, software may query all of the parameters to determine whether or not each is valid, e.g., that a value has been input or an inputted value is within an acceptable range. At step 334, if one or more of the parameters are invalid, software 80 may notify the user and prompt the user for new values. However, if all parameters are valid, at step 338, fringe counting module 82 starts acquiring and processing image data substantially simultaneously with pressurization system control module 86 starting to control the pressure at film window 14 at step 342.

At step 346, fringe counting module 82 may plot in graph frame 104 the average brightness versus either time or pressure for each sampling region 30 immediately after the fringe control module determines the average brightness for each image captured by framegrabber card 90. In addition, analysis module 114, at step 350, may continually analyze each average brightness curve as it is plotted to determine if a maximum or minimum has occurred. At step 354, if a maximum or minimum has occurred, analysis module 114 may display in graph frame 104 an indicator 116, such as a vertical line, corresponding to that maximum or minimum.

At step 358, pressurization system control module 86 may determine whether or not the maximum pressure input via "Maximum Pressure" control 136 or other control has been reached. If not, at step 362, software may determine if user has selected "Stop" button 146. Pressurization system control module 86 may also determine whether or not a leak is occurring, e.g., due to specimen 16 being improperly mounted or film window 14 having ruptured or containing a defect, among other reasons.

If the user has selected "Stop" button 146, at step 366, software notifies user than testing has been stopped. In addition, at step 370, software 80 stops fringe counting module 82 from continuing to collect and process data and stops pressurization system control module 86 from continuing to inflate film window 14. If the user has selected the "Stop" button 146 during testing, it will likely be because there is a problem with specimen 16, parameters and/or sampling region(s) 30. For example, specimen 16 may not be located properly, one or more of the parameters were input incorrectly, the image in image frame 100 may not be optimized and/or the location(s) and/or size(s) of the sampling region(s) 30 is/are not suitable, among others. Accordingly, at steps 374, 378, 382, 386, respectively, the user has the opportunity to determine whether or not the specimen is located properly, the parameters are correct and the sampling regions are acceptable. If these items are okay, the user may then restart the test at step 326. If any one or more of these items are not okay, at steps 390, 394, 398, 402, respectively, the user has the opportunity to, respectively, adjust specimen 16, correct the parameters and select new sampling region(s) 30 and/or change the brightness and/or contrast of the image displayed in image frame 100.

If the user has not selected "Stop" button 146, at step 406, software 80 may determine if user has selected "Pause" button 148. If so, at steps 410, 414, software 80 may notify the user that the software is in a pause mode, which may include fringe counting module 82 stopping its determination of average brightness, analysis module 114 from determining minima and maxima and pressurization system control module 86 from applying pressure to film window 14. Then, at step 418, software 80 may monitor whether or not the user reselects the "Pause" button 144, which may upon first selection change to a "Continue" button (not shown) in a manner know in the art, selects "Start" button 142 or otherwise notifies user interface 28 that the user desires to continue. If the user has not provided such notification, software 80 continues to monitor in pause mode if the user provides such notification. When the user notifies software 80 of the user's desire to continue, the software continues with the test, e.g., by again performing steps 338 et seq.

If the maximum pressure has been reached as determined at step 358, the user may determine at step 422 whether or not the brightness curve(s) 108 plotted in graph frame 104 are acceptable, e.g., by visually inspecting whether or not the locations of maxima and minima indicators 116 determined by analysis module 114 appear to correspond properly to the locations of fringes 34 and nodes 36. If one or more indicators 116 are not located properly and/or missing, e.g., due to local noise spikes discussed above, software 80 may determine at step 426 whether or not the use has selected the "Manual Check" control 152. If not, the user may proceed to steps 374, 378, 382, 386 to determine whether or not, respectively, specimen is located properly, the parameters are correct, the image is optimized and/or sampling regions are acceptable and proceed through one or more of steps 390, 394, 398, 402 before restarting the test. However, if the user has selected "Manual Check" control 152, software may at step 430 allow the user to modify indicators 116 as desired, e.g., in a manner described above or other manner.

At step 434, if the new indicator locations are acceptable to the user, at step 438, output module 88 may determine a displacement, or height, versus pressure curve 172. At step 442, output module 88 may fit a curve 174 to displacement versus pressure curve using either the polynomial selected in "Shape" control 158 or a default curve if the user did not select a polynomial. In addition, at step 446, output module 88 may also determine various material properties, such as Young's modulus and prestress. At step 450, if the user desires to view the results on monitor 74, the user may select "Display" button 166 or other control for displaying the results, e.g., in results window 168 at step 454. If not, the results may be written to an output file for later viewing and/or manipulation. At step 458, if the user desires to conduct a new test, the user may proceed back to step 302. If not, at step 462, user may exit the user interface in a manner known in the art. If at step 422, user is satisfied with each average brightness curve 30, software 80 may proceed directly to step 438 and subsequent steps. If at step 434 the new locations of indicators 116 are not acceptable, the user may proceed to steps 374, 378, 382, 386 and corresponding steps 390, 394, 398, 402 to correct problems with specimen 16, parameters, the image and/or sampling regions 30.

Those skilled in the art will appreciate that flow diagram 300 is merely illustrative of the present invention, and that the steps described may be performed in different order and/or may be replaced and/or supplemented with other steps and that some steps may be eliminated, depending upon the application of the present invention. Similarly, those skilled in the art will recognize that the functionalities relating to the various steps described above may be implemented in many ways other than described. Therefore, an exhaustive recitation of these alternatives is deemed unnecessary.

While the present invention has been described in connection with a preferred embodiment, it will be understood that it is not so limited. On the contrary, it is intended to cover all alternatives, modifications and equivalents as may be included within the spirit and scope of the invention as defined above.

What is claimed is:

1. A system for determining the movement of fringes and/or nodes of an interference pattern, comprising:
    a detection device for capturing an image of the interference pattern;
    a user interface in communication with said detection device for displaying to a user said image;
    a first module that allows a user to interactively select at least one sampling region from said image; and
    a second module that determines the passage of at least one of the fringes and nodes of the interference pattern through said at least one sampling region.
2. A system according to claim 1, wherein said first module allows a user to select the shape of said at least one sampling region.
3. A system according to claim 1, wherein said first module allows a user to selected the size of said at least one sampling region.
4. A system according to claim 1, wherein said first module allows a user to select at least two sampling regions and said second module determines the passage of at least one of the fringes and nodes through each of said at least two sampling regions.
5. A system according to claim 4, wherein said first module allows a user to select the shape of each of said at least two sampling regions.
6. A system according to claim 4, wherein said first module allows a user to selected the size of each of said at least two sampling regions.
7. A system according to claim 1, wherein said second module determines the average brightness of said image in said at least one sampling region.
8. A system according to claim 1, further comprising a third module that graphically displays to a user the passage of at least one of the fringes and nodes through said at least one sampling region.
9. A system according to claim 8, wherein said third module displays an average brightness versus time or pressure curve corresponding to said at least one sampling region.
10. A system according to claim 4, further comprising a third module that graphically displays to a user the passage of at least one of the fringes and nodes through each of said at least two sampling regions.
11. A system according to claim 10, wherein said third module displays an average brightness versus time or pressure curve for each of said at least two sampling regions.
12. A system according to claim 1, further comprising:
    a third module that displays a curve representing the movement of fringes and nodes of the interference through the at least one sampling region;
    a fourth module that analyzes at least one characteristic of said curve and displaying to a user a result of said analysis; and
    a fifth module that allows a user to interactively change said result.
13. A system according to claim 4, further comprising:
    a third module that displays a curve for each of said at least two sampling regions representing the movement of fringes and nodes of the interference through the corresponding one of said at least two sampling regions;
    a fourth module that analyzes at least one characteristic of each of said curves and displaying to a user a result of said analysis; and
    a fifth module that allows a user to interactively change said result.
14. A system according to claim 1, wherein said detection device is a digital camera.
15. A system for determining the movement of fringes and nodes of an interference pattern through at least one sampling region, comprising:
    a first module that displays at least one curve representing the movement of fringes and nodes of the interference through the at least one sampling region;
    a second module that analyzes at least one characteristic of said curve and displays to a user a result of said analysis; and
    a third module that allows a user to interactively change said result.
16. A system according to claim 15, wherein said second module determines the location on said curve of at least one maximum or minimum and displays to a user said location.
17. A system according to claim 16, wherein said second module displays a first visual indicator at said location.
18. A system according to claim 17, wherein said third module allows a user to move said first visual indicator.
19. A system according to claim 17, wherein said third module allows a user to add a second visual indicator.
20. A system according to claim 18, wherein said third module allows a user to remove said first visual indicator.
21. A system according to claim 15, wherein said second module displays on said curve a first visual indicator corresponding to said at least one characteristic of said curve.
22. A system according to claim 21, wherein said third module allows a user to move said first visual indicator.

23. A system according to claim 21, wherein said third module allows a user to add a second visual indicator.

24. A system according to claim 21, wherein said third module allows a user to remove said first visual indicator.

25. A system according to claim 15, wherein said first module displays at least two curves corresponding to corresponding one of a plurality of sampling regions.

26. A system according to claim 25, wherein said second module analyses each of said at least two curves and displays results for each.

27. A system according to claim 26, wherein said third module allows a user to manipulate said result for each of said at least two curves.

28. A system according to claim 15, further comprising a fourth module for using said results as modified by a user.

29. A system according to claim 28, wherein the system determines a displacement of a structure and said fourth module calculates the displacement.

30. A method of determining the movement of fringes and/or nodes of an interference pattern, comprising the steps of:
    capturing an image of the interference pattern;
    displaying said image on a display device; and
    interactively selecting at least one sampling region from said image displayed on said display device.

31. A method according to claim 30, wherein the step of capturing said image includes capturing said image with a digital camera.

32. A method according to claim 30, wherein the step of displaying said image on said display device includes displaying said image on a computer monitor.

33. A method according to claim 30, wherein the step of interactively selecting at least one sampling region includes selecting at least two sampling regions.

34. A method according to claim 30, wherein the step of interactively selecting at least one sampling region is performed using a pointing device.

35. A method according to claim 34, wherein said pointing device is a mouse.

36. A method according to claim 30, wherein the step of interactively selecting at least one sampling region includes selecting the location of said at least one sampling region.

37. A method according to claim 30, wherein the step of interactively selecting at least one sampling region includes selecting the size of said at least one sampling region.

38. A method according to claim 30, wherein the step of interactively selecting at least one sampling region includes selecting the shape of said at least one sampling region.

39. A method of determining the movement of fringes and nodes of an interference pattern through at least one sampling region, comprising the steps of:
    displaying at least one curve representing the movement of fringes and nodes of the interference pattern through the at least one sampling region;
    analyzing the at least one characteristic of said curve;
    displaying to a user a result of said analysis; and
    allowing a user to interactively change said result.

40. A method according to claim 39, wherein the step of analyzing the at least one characteristic of said curve includes determining the locations of maxima and minima.

41. A method according to claim 40, wherein the step of displaying to a user said result of said analysis include displaying in conjunction with said curve a visual indicator corresponding to each location of said maxima and minima.

42. A method according to claim 39, wherein the step of displaying to a user said result of said analysis includes displaying in conjunction with said curve a plurality of visual indicators.

43. A method according to claim 39, wherein the step of allowing a user to interactively change said result includes allowing a user to move at least one visual indicator.

44. A method according to claim 39, wherein the step of allowing a user to interactively change said result includes allowing a user to add at least one visual indicator.

45. A method according to claim 39, wherein the step of allowing a user to interactively change said result includes allowing a user to delete at least one visual indicator.

46. A bulge testing system for testing a thin film window, comprising:
    an interferometer for providing an interference pattern;
    an image detector for detecting an image of said interference pattern;
    a display device in communication with said image detector for displaying said image of the interference pattern; and
    a user interface for allowing a user to interactively select at least one sampling region from said image displayed on said display device.

47. A bulge testing system according to claim 46, wherein said image displayed on said display device includes the entire thin film window.

48. A bulge testing system according to claim 46, wherein said user interface allows a user to select the shape of said at least one sampling region.

49. A bulge testing system according to claim 46, wherein said user interface allows a user to selected the size of said at least one sampling region.

50. A bulge testing system according to claim 46, wherein said user interface allows a user to select at least two sampling regions.

51. A bulge testing system according to claim 50, wherein said user interface allows a user to select the shapes of each of said at least two sampling regions.

52. A bulge testing system according to claim 50, wherein said user interface allows a user to selected the size of each of said at least two sampling regions.

53. A bulge testing system for testing a thin film window, comprising:
    an interferometer for providing an interference pattern having fringes and nodes;
    a detector for detecting the movement of said fringes and said nodes at a sampling region;
    a display device in communication with said detector for displaying a curve representing the passage of said fringes and said nodes through said sampling region; and
    a user interface for analyzing at least one characteristic of said curve and displaying a result of said analysis on said display device; and
    a module for allowing a user to interactively change said result.

54. A bulge testing system according to claim 53, wherein said detector is an image detector.

55. A bulge testing system according to claim 54, wherein said image detector is a digital camera.

56. A bulge testing system according to claim 53, wherein said user interface determines a location on said curve of at least one maximum or minimum and displays to a user said location.

57. A bulge testing system according to claim 56, wherein said user interface displays a first visual indicator at said location.

58. A bulge testing system according to claim 57, wherein said module allows a user to move said first visual indicator.

59. A bulge testing system according to claim 57, wherein said module allows a user to add a second visual indicator.

60. A bulge testing system according to claim 57, wherein said module allows a user to remove said first visual indicator.

61. A bulge testing system according to claim 53, further comprising a second module for using said result as modified by a user.

62. A system of determining the movement of fringes and/or nodes of an interference pattern displayed on a display device, comprising:

- a first means for capturing an image of the interference pattern;
- a second means for displaying said image on the display device; and
- a third means for interactively selecting at least one sampling region from said image displayed on the display device.

63. A computer readable medium containing a method executed on a computer for determining the movement of fringes and/or nodes of an interference pattern displayed on a display device, the method comprising the steps of:

- capturing an image of the interference pattern;
- displaying said image on the display device; and
- allowing a user to interactively select at least one sampling region from said image displayed on the display device.

* * * * *